United States Patent
Skinner et al.

(10) Patent No.: US 7,961,322 B2
(45) Date of Patent: *Jun. 14, 2011

(54) METHOD FOR CONDITIONAL APPLICATION OF COLOR MEASUREMENT ERROR COMPENSATION IN SPECTRAL SENSORS

(75) Inventors: Gary W. Skinner, Rochester, NY (US); Lalit Keshav Mestha, Fairport, NY (US); Paul S. Bonino, Ontario, NY (US)

(73) Assignee: Xerox Corporation, Norwalk, CT (US)

( * ) Notice: Subject to any disclaimer, the term of this patent is extended or adjusted under 35 U.S.C. 154(b) by 329 days.

This patent is subject to a terminal disclaimer.

(21) Appl. No.: 12/203,520

(22) Filed: Sep. 3, 2008

(65) Prior Publication Data
US 2009/0296091 A1  Dec. 3, 2009

Related U.S. Application Data

(60) Provisional application No. 61/056,090, filed on May 27, 2008.

(51) Int. Cl.
*G01J 3/50* (2006.01)
(52) U.S. Cl. .......... 356/402; 702/182; 702/196
(58) Field of Classification Search .......... 356/402
See application file for complete search history.

(56) References Cited

U.S. PATENT DOCUMENTS

| | | |
|---|---|---|
| 6,384,918 B1 | 5/2002 | Hubble, III et al. |
| 6,556,932 B1 | 4/2003 | Mestha et al. |
| 6,584,435 B2 | 6/2003 | Mestha et al. |
| 6,587,793 B2 | 7/2003 | Viassolo et al. |
| 6,721,692 B2 | 4/2004 | Mestha et al. |
| 6,975,949 B2 | 12/2005 | Mestha et al. |
| 7,259,853 B2 | 8/2007 | Hubble, III et al. |
| 7,271,910 B2 | 9/2007 | Paul et al. |
| 7,277,196 B2 | 10/2007 | Van de Capelle et al. |
| 7,333,208 B2 | 2/2008 | Mestha et al. |
| 7,684,082 B2 | 3/2010 | Mestha et al. |
| 7,768,682 B2 | 8/2010 | Mestha et al. |
| 7,773,222 B2 | 8/2010 | Mestha |
| 2006/0152718 A1 | 7/2006 | Mestha et al. |
| 2009/0009766 A1 | 1/2009 | Bonino et al. |
| 2009/0296107 A1 | 12/2009 | Mestha et al. |
| 2009/0296108 A1 | 12/2009 | Gil et al. |
| 2009/0296110 A1 | 12/2009 | Mestha et al. |
| 2009/0299905 A1 | 12/2009 | Mestha et al. |

*Primary Examiner* — F. L Evans
(74) *Attorney, Agent, or Firm* — Fay Sharpe LLP

(57) ABSTRACT

Color measurements of color samples are estimated by a system and method wherein an area coverage of a color sample is computed, the color sample is printed, a color of the printed color sample, such as a set of reflectance values, is measured at a first temperature, and a color of the printed color sample is estimated at a second temperature lower than the first temperature, the estimation being based on the area coverage and a thermochromatic model which represents relationships between measured colors of printed color samples at the first and second temperatures.

21 Claims, 8 Drawing Sheets

US 7,961,322 B2

METHOD FOR CONDITIONAL APPLICATION OF COLOR MEASUREMENT ERROR COMPENSATION IN SPECTRAL SENSORS

This application claims the priority of U.S. Provisional Application Ser. No. 61/056,090, filed May 27, 2008, the disclosure of which is incorporated herein in its entirety by reference.

CROSS REFERENCE TO RELATED PATENTS AND APPLICATIONS

The following copending applications, the disclosures of which are incorporated in their entireties by reference, are mentioned:

U.S. patent application Ser. No. 12/017,746 (now U.S. Pat. No. 7,768,682), filed Jan. 22, 2008, entitled METHOD AND APPARATUS FOR OPTIMUM BLACK COMPONENT DETERMINATION FOR GRAY COMPONENT REPLACEMENT, by Mestha, et al.;

U.S. patent application Ser. No. 12/127,643 (U.S. Publication No. 2009/0296107), filed May 27, 2008, entitled METHOD, APPARATUS AND SYSTEMS TO RETRIEVE GCRS FROM HISTORICAL DATABASE, by Mestha, et al.;

U.S. Patent Application Ser. No. 61/056,189 (parent of U.S. Publication No. 2009/0296110), filed May 27, 2008, entitled IMAGE INDEXED RENDERING OF IMAGES FOR TUNING IMAGES FROM SINGLE OR MULTIPLE PRINT ENGINES, by Mestha, et al.;

U.S. Patent Application Ser. No. 61/056,095 (parent of U.S. Publication No. 2009/0009766), filed May 27, 2008, entitled METHOD TO MINIMIZE INSTRUMENT DIFFERENCES IN COLOR MANAGEMENT FUNCTIONS, by Bonino, et al.;

U.S. Patent Application Ser. No. 61/056,102 (parent of U.S. Pat. No. 7,773,222), filed May 27, 2008, entitled UV ENHANCED FULL WIDTH ARRAY SCANNING SPECTROPHOTOMETER, by Mestha;

U.S. patent application Ser. No. 11/737,576 (now U.S. Pat. No. 7,684,082), filed Apr. 19, 2007, entitled METHOD AND SYSTEM FOR COMPENSATING FOR THERMOCHROMATICITY DIFFERENCES IN INLINE SPECTROPHOTOMETERS, by Mestha, et al., U.S. patent application Ser. No. 12/127,719 (U.S. Publication No. 2009/0296108), filed May 27, 2008, entitled COOPERATIVE NEIGHBOR PRINTING SYSTEM PROFILE METHODS AND SYSTEMS, by Gil, et al.; and U.S. patent application Ser. No. 12/127,649 (U.S. Publication No. 2009/0299905), filed May 27, 2008, entitled A WEB ENABLED COLOR MANAGEMENT SERVICE AND METHOD, by Mestha, et al.

BACKGROUND

The exemplary embodiment relates to the color management arts and finds particular application in connection with a system and method for printer color modeling which compensates for the influence of temperature on sensed values by taking into account area coverage of a sensed region.

Customers have come to expect a high image quality in color documents generated on electrostatographic (xerographic) image rendering devices, such as printers and copiers. One of the elements that affect the perception of image quality is an ability to consistently produce the same quality image output on a printer from one day to another, from one week to the next, month after month. Consistency between the outputs of different printers is also expected. Color rendering devices tend to exhibit a drift in their output over time, due to normally expected operational variations, such as temperature and humidity variations, system aging, and the like. Accordingly, such devices are calibrated frequently with the objective of maintaining consistent and accurate color outputs.

In-line spectrophotometric measuring systems for sensing reflectance indicative of the colors produced by the color rendering device have been developed for automated printer calibration and a variety of other color management applications. Such spectral sensors are often positioned to measure reflectance of marked sheets of print media shortly after they have been fused. Since fusing is the final step of the xerographic process, the fuser is usually located next to the paper output of the printer. Therefore due to physical constraints and space availability, the sensor is often located close to the fuser. The print media and fused colorants (typically toners) are therefore still at a temperature above ambient when the sensor measurements take place. The fused print media may remain at an elevated temperature for several minutes, so that, even in the stacker, the sheets are still at an elevated temperature. It has been found that the colors of the "hot" print media generated from the sensor measurements differ from those obtained under ambient conditions. The difference has been attributed to thermo-chromatic material properties, i.e. the toner colors shift as a function of temperature. This limits the potential accuracy of the in-line spectrophotometer since it will never "see" the printed media under the same conditions as the customer. It is desirable to provide an estimate of the color as it would be perceived by the customer at ambient temperatures.

Recent data from operational studies of in-line spectrophotometric systems suggest that color measurement differences occur between colors, when measured at the embedded location, with respect to similar measurements of the same prints made at ambient temperature. Such color measurement differences can be responsible for significant accuracy errors between the ultimately desired output color and the actual output color. Empirically-determined error differences (deltaE, or dE*) can be computed, e.g., in a range between a measurement at 60° C. and an ambient temperature of 22° C.

Mathematical methods have been developed to correct this thermo-chromatic error. One method involves building a mathematical model, implemented in the form of a thermo-chromaticity compensation matrix that relates thermo-chromatically shifted (hot) colors to thermo-chromatically stable (cool) colors. This matrix is then applied as a signal processing function to subsequent in-line color measurements, thus producing a final spectral measurement that closely approximates the stable (cool) color.

It has now been found that a global application of the single compensation matrix to all colors which assumes a linear relationship between hot and cool colors can result in errors in some regions while providing improvements to other regions.

There remains a need for a system and method for compensating for thermochromaticity errors which overcomes these problems.

INCORPORATION BY REFERENCE

The following references, the disclosures of which are incorporated herein in their entireties by reference, are mentioned:

U.S. application Ser. No. 11/737,576 (now U.S. Pat. No. 7,684,082), filed Apr. 19, 2007, entitled METHOD AND SYSTEM FOR COMPENSATING FOR THERMOCHRO- MATICITY DIFFERENCES IN INLINE SPECTROPHO-TOMETERS, by Mestha, et al., discloses a method for color measurement of a color output device. Output colors of the device vary in color during a time of cooling from a just-fused temperature to an ambient temperature. The variance in color is represented by a thermochromatic model. The method includes measuring in situ color of a print output of the color output device at a first temperature, converting the measured in situ color to a corresponding output ambient color from the thermochromatic model, and using the converted desired output ambient color as a basis for assessing operability of the color output device.

U.S. Pat. No. 6,721,692, entitled SYSTEMS AND METHODS FOR DETERMINING SPECTRA USING DYNAMIC LEAST SQUARES ALGORITHMS WITH MEASUREMENTS FROM LED COLOR SENSOR, by Mestha, et al., discloses a method of determining a reflectance spectrum. The method includes obtaining a normalized value from a plurality of illuminant sensor outputs, each illuminant sensor output indicating a reflectance value obtained from a target. Reference data is obtained from a reference database that correlates reference spectra with a corresponding plurality of normalized illuminant sensor outputs for reference colors. The reference data includes data in a neighborhood of each reflectance value. A spectrum S is determined, based on the illuminant sensor outputs and the reference data which places greater importance on the data in the neighborhood of each reflectance value.

U.S. Pat. No. 6,384,918, entitled SPECTROPHOTOMETER FOR COLOR PRINTER COLOR CONTROL WITH DISPLACEMENT INSENSITIVE OPTICS, by F F. Hubble, III, et al., discloses a color correction system for a color printer in which a spectrophotometer is mounted in the output path of a printer for sensing the colors of a test patch printed on a test sheet. A sequential actuation circuit sequentially illuminates the test patch with different illumination colors. The spectrophotometer is mounted at one side of the printer output path and has a lens arrangement allowing it to be substantial insensitive to variations in a displacement between the spectrophotometer and the test sheets.

U.S. Pat. No. 6,975,949, entitled FULL WIDTH ARRAY SCANNING SPECTROPHOTOMETER, by L. K. Mestha, et al., discloses a full width array spectrophotometer for full width scanning color analysis of a printed print media sheet. The spectrophotometer includes linear arrays of LEDs in a repeating pattern to span the paper path and a corresponding parallel array of photodetectors to receive light reflected from a transverse illuminated band extending transversely across a print media sheet moving in the paper path.

U.S. Pat. No. 7,333,208, entitled FULL WIDTH ARRAY MECHANICALLY TUNABLE SPECTROPHOTOMETER, by L. K. Mestha, et al., discloses a method of full transverse scanning color analysis of color printed sheets moving in a color printer path with a full width array spectrophotometer.

U.S. Pat. No. 7,271,910, entitled SYSTEMS AND METHODS FOR COMPENSATING FOR TEMPERATURE INDUCED SPECTRAL EMISSION VARIATIONS IN LED BASED COLOR PARAMETER MEASURING DEVICES, by P. Paul, et al., discloses a method of determining color parameter values for sensors using a reference database containing different model information for different temperatures. The method includes determining an appropriate model for the operating temperature and the outputs of the sensor and determining color parameter values based on the determined model.

U.S. Pat. No. 7,259,853, entitled SYSTEMS AND METHODS FOR AUGMENTING SPECTRAL RANGE OF AN LED SPECTROPHOTOMETER, by F. F. Hubble III, et al., discloses an LED spectrophotometer device for determining an aspect of the color of an object. The device includes a visible spectrophotometer comprising a plurality of light emitting diodes that emit light in the visible spectrum onto the object. At least one detector detects the light after being directed onto the object and for generating an output. A UV light emitting diode assembly emits light in the near ultraviolet spectrum and communicates with at least one detector for generating an output. A mechanism blocks light outside of a preselected visible blue spectral range from being detected by the detector of the UV light emitting diode assembly.

U.S. Pat. No. 6,587,793, entitled SYSTEMS AND METHODS FOR DETERMINING SPECTRA USING FUZZY INFERENCE ALGORITHMS WITH MEASUREMENTS FROM LED COLOR SENSOR, by Viassolo, et al. discloses a method of determining a reflectance spectrum, which includes obtaining a normalized value from a plurality of illuminant sensor outputs, each illuminant sensor output indicating a reflectance value obtained from a target, obtaining reference data from a reference database that correlates reference spectra with a corresponding plurality of normalized illuminant sensor outputs for reference colors, and determining a spectrum S based on the illuminant sensor outputs and the reference data, wherein the determining step comprises generating a non-linear model.

U.S. Pat. No. 6,934,053, issued Aug. 23, 2005 to L. K. Mestha, et al., entitled METHODS FOR PRODUCING DEVICE AND ILLUMINATION INDEPENDENT COLOR REPRODUCTION, describes a method for obtaining spectrally matched color outputs using data from a real-time sensor, such as, for example, a spectrophotometer on the output trays of a marking device.

U.S. Pub. No. 2006/0244968, published Nov. 2, 2006, entitled METHOD TO AUTOMATICALLY IDENTIFY AND COMPENSATE FOR SUBSTRATE DIFFERENCES USING A SENSOR, by L. K. Mestha, et al., discloses a method of calculating the degree of similarity between the test media substrate and pre-characterized substrates stored in a broad media database by using from the sensor measurements some measured media attributes (e.g., spectral reflectance of the substrate, special characteristics such as media fluorescence, other non-color-related attributes such as surface roughness, weight, thickness, gloss, etc.).

BRIEF DESCRIPTION

In accordance with one aspect of the exemplary embodiment, a method for estimating color measurements of color samples includes computing an area coverage of a color sample, printing the color sample, measuring a color of the printed color sample at a first temperature, estimating a color of the printed color sample at a second temperature lower than the first temperature, the estimation being based on the area coverage and a thermochromatic model which represents relationships between measured colors of printed color samples at the first and second temperatures.

In accordance with another aspect, a thermochromaticity compensation system includes a spectral sensor which measures colors of printed color samples at a first temperature. Memory stores a thermochromatic model which represents relationships between measured colors of printed color samples at the first temperature and measured colors of printed color samples at a second temperature as a function of a computed area coverage. A processor receives a measured color of a printed color sample from the spectral sensor at the first temperature, computes area coverage of the printed color sample, and accesses the model to estimate a color of the printed color sample at the second temperature based on the measured color and computed area coverage.

In accordance with another aspect, an algorithmic method to compensate for thermochromaticity errors of in situ spectral color measurements of a color printing device is provided. The method includes obtaining spectral measurements at a plurality of computed area coverage values of printed colors generated by the color printing device measured at a first temperature by an in-line spectrophotometer and at a second temperature. A model is generated, based on the spectral measurements, which maps spectral measurements at the first temperature to spectral measurements at the second temperature, as a function of area coverage. The method further includes measuring a selected color corresponding to a color input signal representing a desired color at the second temperature, wherein the selected color is measured at the first temperature by the in-line spectrophotometer, computing an area coverage of the selected color, applying the model to convert the measured color to a corresponding color when the measured color changes to the second temperature, based on the area coverage.

DETAILED DESCRIPTION

Figure 1:
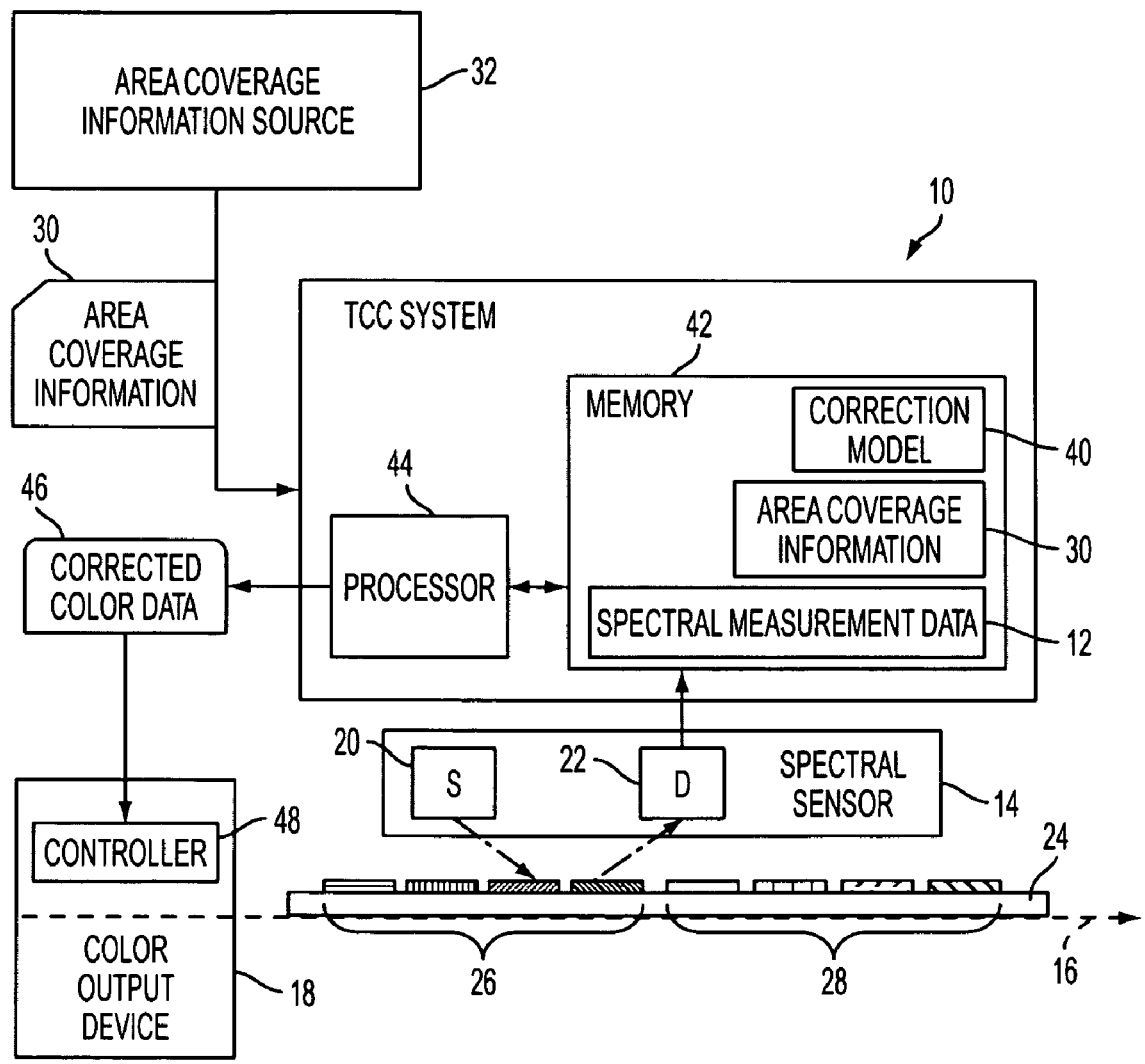
FIG. 1 is a functional block diagram of an exemplary thermochromaticity correction system in accordance with one aspect of the exemplary embodiment.

Aspects of the exemplary embodiment relate to a system and method for thermochromaticity correction which finds application in automated printer calibration and other color management applications. Thermochromaticity correction, as used herein, implies a correction which is applied to account for thermochromatic material properties, in particular, the shift in toner colors as a function of temperature.

U.S. application Ser. No. 11/737,576 (now U.S. Pat. No. 7,684,082) discloses a system and method which includes sensing reflectance values with an in-line spectral sensor and correcting the values by applying a global thermochromaticity correction. According to aspects illustrated therein, there is provided an algorithmic method to compensate for thermochromatic differences of in situ spectral color measurement systems within a color printed device. A mapping model is made from empirical data comprising the differences between spectral measurements of a printed color generated by the color printing device at a first temperature and a second temperature. The spectrophotometric sensor measures a generated color at an embedded location where the measurement occurs at about the first temperature. The mapping determines what color will result when the temperature cools to the ambient or second temperature. System performance is then assessed based on the predicted, map-determined cool color. The method of U.S. Pat. No. 7,684,082 can be adapted to provide a TCC system and method as disclosed herein which account for area coverage effects.

Experimental data has shown that while favorable results can be achieved with this method for color patches with high toner area coverage (density), in some instances the measurements of lower density patches are less likely to benefit from the correction. The present embodiment provides a system and method which factors area coverage into the thermochromaticity correction and thus applies a non-uniform correction to the sensed reflectance values.

In the exemplary spectrophotometric color measurement system disclosed herein, a first spectral sensor, such as an in-line spectral sensor in the output path of a color output device, measures colors at a first temperature, typically hot, at an embedded "just-fused" location in the output path of a color printer. A thermochromatic correction system (TCC) relates the measured colors to an output color at a second temperature, e.g., a cooled ambient temperature. The measured color is converted via a thermochromatic model, to a corrected color which is expected for the measured color in response to a particular input signal, thereby providing a real time conversion to the anticipated output color when cooled to the ambient temperature. The exemplary TCC model takes into account area coverage as well as temperature difference in generating the corrected color. Printer operability can be assessed by verifying predicted color accuracy or by adjusting the input signal to compensate for a measured difference between the anticipated output color and an actually measured ambient temperature color.

An in-line spectrophotometer which may be used as the in-line spectral sensor in the present system is generally a high speed color-measuring device that illuminates a color sample of interest with a light source, measures light reflected from the sample and interprets the results as a reflectance spectrum across a specific range of wavelengths. The exemplary spectrophotometer is mechanically integrated (embedded) into the paper path of a color output device, such as a color printer or copier, and is therefore capable of measuring color on paper immediately after printing, i.e., before the paper leaves the printing device. The in-line spectral sensor may be positioned in the output path of the color output device intermediate a marking engine, which generates a printed color sample to be measured, and a finisher of the color output device, which is downstream of the marking engine and connected thereto by a paper path. An exemplary in-line spectrophotometer which may be used is a full width array (FWA) spectrophotometer as described in U.S. Pat. No. 6,975,949, the disclosure of which is incorporated herein in its entirety, by reference. Such a spectrophotometer includes a full-width array of LEDs of a multiplicity of different colors arranged in a repeating pattern which are selectively actuated to illuminate the sheet with the different colors in combination with a full width scanning bar comprising an array of photodiodes which detect the reflected light. Similar page-scanning mechanisms may alternatively be used.

The color samples tested may be test patches, i.e., generated by separately printing a set of different, predefined colors in small localizable regions of the print media. In other embodiments, the samples may be customer images or selected regions thereof. In the case of customer images, the customer image may be examined to identify an area of relatively consistent color.

It is postulated that areas of high toner coverage do not cool as quickly as areas of lower toner coverage. Thus, it is expected that a high area coverage sample will be at a higher temperature, at the time it is seen by the in-line spectrophotometer, than a lower area coverage sample. It has been found experimentally that area coverage does impact the measurement data. By factoring in the area coverage, the applied thermochromaticity corrections can more accurately compensate for these differences.

The area coverage is a way of expressing the density of toner on the sample being tested. It may be expressed, for example as a function of the pixel colorant values of the color separations which are to be applied. Thus for example, in a cyan, magenta, yellow and black system (CMYK, i.e., four color separations) pixel colorant values for each color separation are typically expressed in the range of 0-255, where 255 represents 100%. These colorant values may be normalized, for convenience, to a scale of 0-1. An area coverage can then be computed as a function of the four colorant values, e.g., as an (optionally weighted) sum for a fixed area of the test sample. For example, when colorant values of C, M, and Y are each 127 (50%), and K is 0, these values may be normalized to 0.5, 0.5, 0.5, and 0, respectively, and a computed area coverage may be their sum, i.e., 1.5. The computed area coverage can then be used in generating thermochromaticity corrections. Alternatively, the area coverage of the patches can be estimated using a system as described in U.S. Pat. No. 4,553,033, issued Nov. 12, 1985, to Hubble, entitled INFRARED REFLECTANCE DENSITOMETER, which provides an electrical signal representative of the amount of toner particles on the photosensitive surface of a color output device. Another method of computing area coverage is to compute them from measurements obtained from the spectrophotometer, for example, using the method described in U.S. Pat. No. 7,110,142, entitled SYSTEMS AND METHODS FOR SENSING MARKING SUBSTRATE AREA COVERAGE USING A SPECTROPHOTOMETER, by L. K. Mestha, et al. The spectrophotometer may be the same spectrophotometer which is used for obtaining hot (or clod) measurements, or a different spectrophotometer.

In general, the effect on the thermochromaticity correction will be different for a first area coverage (high density) than for a second area coverage (low density) which is lower than the first area coverage. This is because the variation between the hot and cool measurements generally increases with increasing area coverage.

The problem occurs because the same output color (as measured by a spectral sensor on the cooled color sample) can be created with different levels of toner coverage. Thus, for example, a color generated when colorant values of C, M, and Y are each 127 (50%), may be very similar to the color generated when C, M, and Y are each 140 (55%).

In various aspects, the exemplary method includes building a mathematical model which relates thermochromatically shifted (hot) colors to corresponding thermo-chromatically stable (cool) colors. The model can then be used to correct subsequent sensed colors.

With reference to FIG. 1, a block diagram of an exemplary TCC system 10 is shown. System 10 receives, as input, color measurement data 12 from a first spectral sensor 14, such as an in-line sensor. The spectral sensor 14 is positioned closely adjacent to the output paper path 16 of a color output device 18 and includes an illumination source or more typically, a set of illumination sources S 20 and a detector or set of photodetectors D 22. Exemplary sources 20 and detectors 22 may be arranged in one or more linear arrays, generally in a cross process direction, i.e., perpendicular to the paper path 16, as described, for example, in U.S. Pat. No. 6,975,949. Print media 24 is conveyed on the paper path 16 in the direction shown and passes by the sensor 14 where it is illuminated. The print media can be formed of paper, plastic, cloth, or other flexible material suited to printing. Sets of color samples 26, 28 printed on the print media 24 by the color device 18, at, for example, high and low area coverage, respectively, pass by the detectors 22 as the sheets 24 are conveyed along the path 16. The sources 20 illuminate the printed media and reflected light is sensed by the detectors 22 as reflectance measurements at a plurality of wavelengths ("hot" measurements).

The TCC system 10 further receives, as input, area coverage information 30 from a source 32 of area coverage information, such as the digital front end (DFE) of the color output device. Alternatively or additionally, the source 32 may be a densitometer which is positioned to make density-related measurements on the printed patches and compute an average area coverage for each patch therefrom.

The TCC system 10 includes a thermochromaticity correction model 40. The model 40, along with the color measurement data 12 and area coverage information 30 may be stored in memory 42. A processor 44, having access to the memory 42, inputs the acquired color measurement data 12 and area coverage information to the model 40 to generate corrected color data 46 (estimated "cool" measurements), which is output from the system 10. The TCC system may thus execute instructions which, for each of a set of color samples, e.g., test patches, determine a correction which is based, at least in part, on the area coverage information 30 for that particular sample and which apply the correction to the "hot" measurements. In particular, the area coverage information 30 may be used to identify an appropriate matrix in the model 40 to be applied to the color measurement data 12 which bests fits the area coverage or used as an input to a multidimensional model in which area coverage is a factor.

The corrected color data 46 may be input to an automatic color balance controller 48 for the printing system 18. The automatic color balance control system 48 produces multi-dimensional LUT (Look-Up Table) values for the CMYK primary colors by printing patches, measuring colors and automatically re-adjusting the LUTs until a satisfactory level of accuracy is obtained. While producing spatially adjusted LUTs, the system may automatically lock the printer output to some predetermined color patch targets. The adjustment process may be enabled either by the system controller 48 or by a user with minimal interaction.

Figure 2:
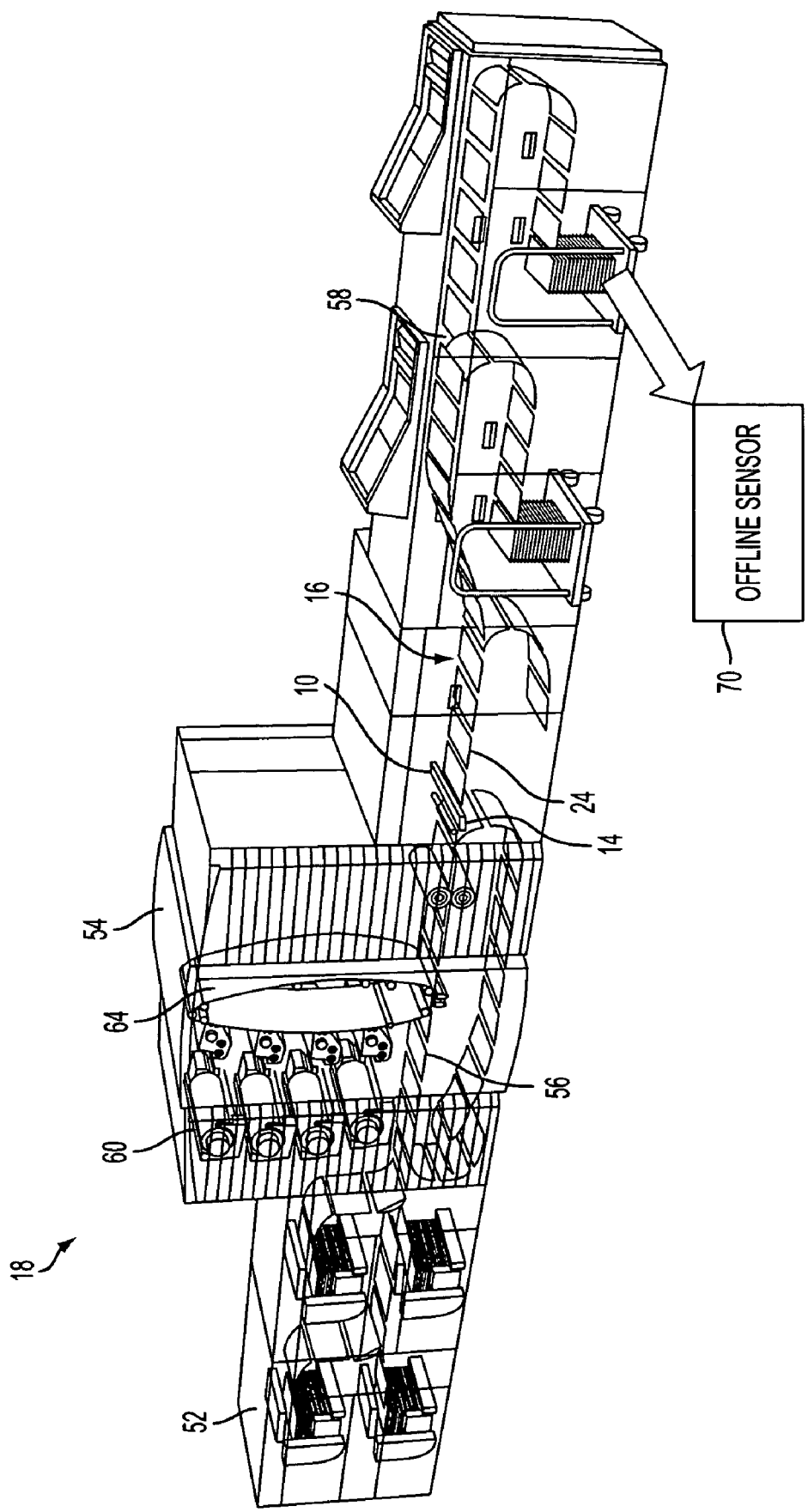
FIG. 2 is an exemplary embodiment of a printing system including an embedded spectrophotometer, thermochromaticity correction system, and illustrating an off-line spectrophotometer, in accordance with another aspect of the exemplary embodiment.

To illustrate the exemplary spectrophotometric color measurement system 10 in situ, FIG. 2 shows an exemplary color output device 18 in the form of a digital color printing device. Printer 18 includes a source 52 of paper or other print media substrate 24, such as a paper feeder. The feeder 52 is connected to a marking engine 54 by a paper path 56, which path includes output path 16 and which connects the marking engine 54 with a finisher 58. As illustrated, the marking engine 54 is a multi-color engine having a plurality of imaging/development subsystems 60, that are suitable for producing individual color images (e.g., with four color separations CMYK) on a photoreceptor 64 in the form of a belt. The belt then transfers the images to the print media substrate 24, here shown as sheets of paper. The first spectral sensor 14, such as a full-width array (FWA) scan bar, measures color values of test patches, either on the belt 64 or on the paper 24. To generate the model 40, the measured color reflectivities of a set, e.g., about 1,000 or 2,000 printed color test patches, at different area coverages, are spatially mapped to corresponding corrected color values measured on the cool (e.g., ambient) test patches by a second spectral sensor 70 and are input to the model. Thereafter, the system 10 can, in real-time, spectrophotometrically measure non-ambient temperature colors, yet maintain accurate ambient color outputs.

While the printing system 18 is described as having four color separations (C, M, Y and K), it is to be appreciated that the fewer or more color separations may be employed in printing the test patches 26, 28, such as 2, 3, 6, or more color separations.

The spectral sensor 14 may output the color values in any convenient color space, such as L*, a*, b*, XYZ, or the like, depending on the desired color description. One suitable spectrophotometer 14 is disclosed in U.S. Pat. No. 6,384,918, the disclosure of which is hereby incorporated by reference. The spectrophotometer disclosed therein is suited to non-contact measurement of colored target areas such as test patches 26, 28 on moving printed test sheets in an output path of a color printer, where test patches may be sequentially angularly illuminated with multiple different colors, and a photosensor providing electrical signals in response. The spectrophotometer includes a lens system for transmitting that reflected illumination (multiple illumination sources comprise approximately eight or more individual LEDs (e.g., light emitting diodes, laser diodes, or organic light emitting devices), from the test patch. The exemplary spectrophotometer provides non-contact color measurements of moving color target areas variably displaced therefrom within normal paper-path baffle spacings.

Figure 3:
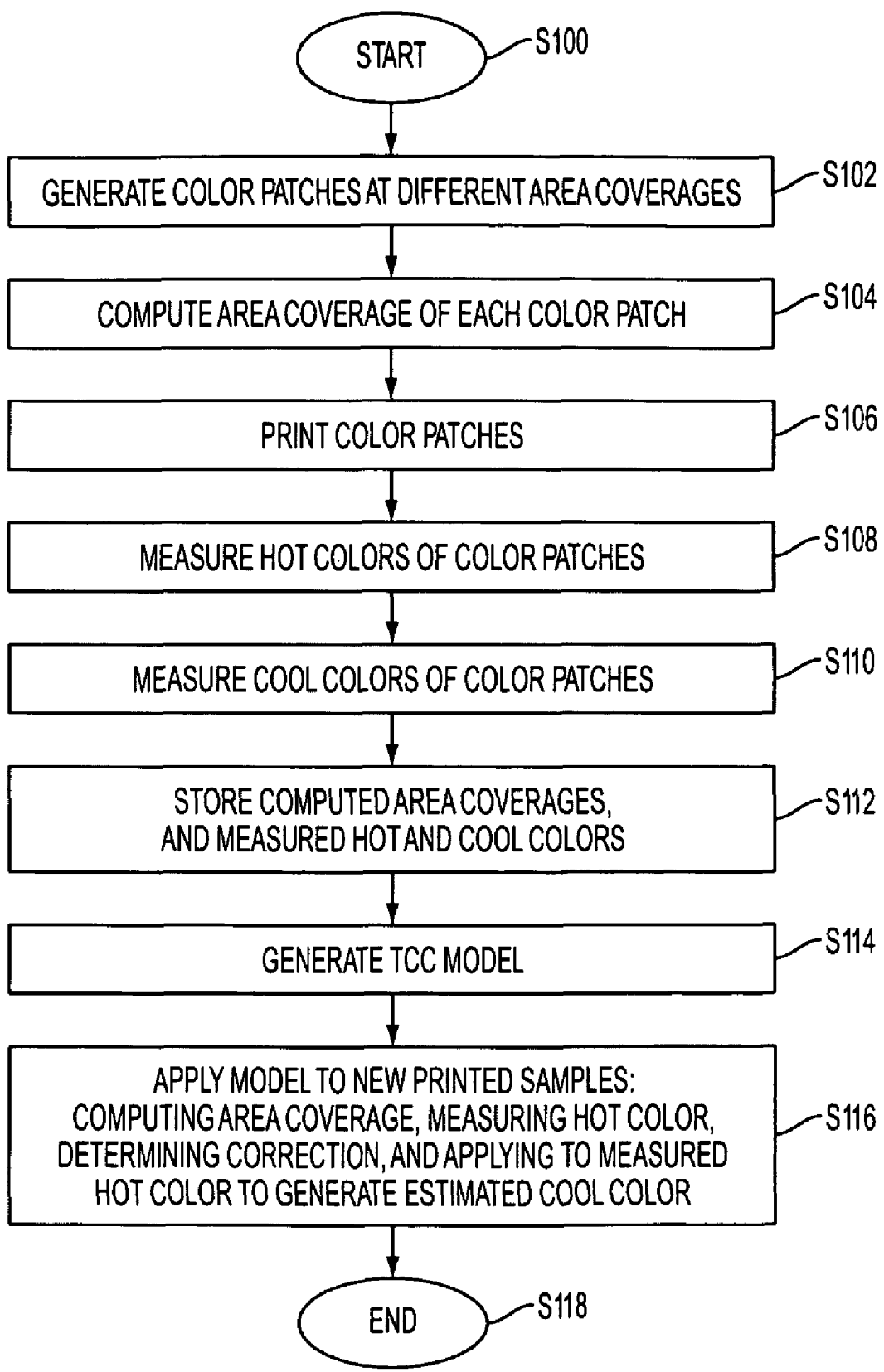
FIG. 3 is a flowchart illustrating a method of correction of in-line color measurements in accordance with another aspect of the exemplary embodiment.

FIG. 3 illustrates the exemplary method. The method begins at S100. At S102, color patches are generated. For example, a set of color patches representing the total color space of interest is generated (e.g., in terms of pixel values for each of the color separations utilized by the device). For example, at least about 300 or at least 2000 patches are generated, including patches corresponding to different levels of area coverage.

At S104, an area coverage of each of the patches to be printed is computed. (This step may be performed later is the area coverage is computed on the toner deposited on the photoreceptor or printed sheets).

At S106, the color patches 26, 28 are printed on print media.

At S108, "hot" measurements on the patches are made. A first set of in situ measurement data is this acquired at a first (hot) temperature with the first spectral sensor 14. Typically, the printed test patches 26, 28 are at a temperature of about 40° C. or higher when they are measured, with the temperature of the patches varying with area coverage The hot temperature of the patches is representative of the temperatures to be expected during normal operation of the color output device.

At S110, "cool" measurements on the same patches 26, 28 are made. For example, the finished prints are collected, cooled and measured again after the color has stabilized, at a second (cool) temperature. The second set of measurement data (cool) can be made with the same in-line spectrophotometer 14 used for the first set of measurements (hot). Or, a different device 70 can be used for these measurements. The temperature selected for the second set (cool) measurements is generally around ambient temperature, such as about 20-25° C., e.g. 22° C.

At S112, the hot and cool measurements and area coverage information may be stored in a training database.

At S114, the first and second sets of measurement data and computed area coverage are used to create a thermochromaticity compensation (TCC) model 40 which can subsequently be used to identify expected cool temperature measurements based on input hot measurements and area coverage. The model may be in the form of a multi-dimensional matrix or a set of compensation matrices.

At S116, the model can then be applied as a signal processing function to subsequent in-line ("hot") color measurements and area coverage information, thus producing a final spectral measurement that closely approximates the stable (cool) color. This step may include computing an area coverage of a sample, which may be a test patch or a portion of a customer image, printing the sample on print media, measuring the hot color of the printed sample, and inputting the hot color and area coverage into the model to obtain an estimated cool color of the printed sample. The method ends at S118.

Step S116 of the method (and other steps if desired) can be fully automated without requiring any manual operations or operator involvement.

Figure 4:
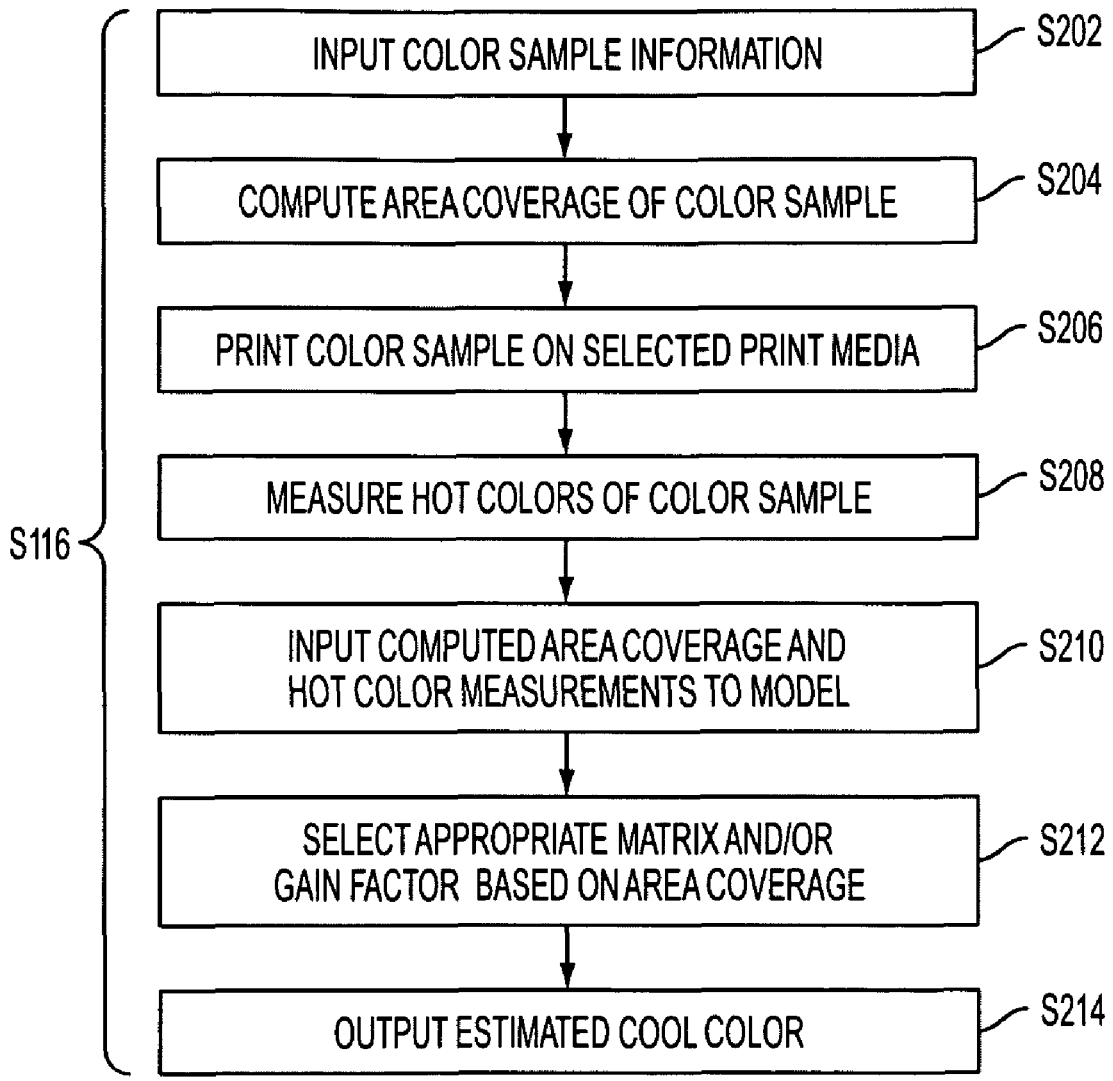
FIG. 4 illustrates substeps of the exemplary method of FIG. 3 for applying the model.

FIG. 4 illustrates the substeps which may be performed in S116 of the exemplary method, i.e., once the model 40 has been built. Step S116 may include inputting color information for a color sample to be printed, which may be a test patch or a portion of a customer image (S202). This step may include automatically acquiring the CMYK information for the sample from the DFE of the printer. At S204, an area coverage of the sample is optionally computed (S204) from the input CMYK information by processor 44 (or subsequently, from densitometer readings, as previously noted). At S206, the sample is printed on a selected print media. At S208, the hot color of the printed sample is measured with the first spectral sensor 14, in the manner previously described. At S210, the hot color and area coverage information is input to the model 40, e.g. by the processor 44. At S212, an appropriate matrix and/or gain factor is automatically selected, based on the input information. At S214, the model applies the selected matrix/gain factor to the color measurements and outputs an estimated cool color of the printed sample as it would be measured when cooled. Where the measured color does not coincide with one of the measured colors in the matrix, interpolation can be used. The estimated (corrected) color of the printed color sample (at the second temperature) may be used as a basis for assessing operability of a color output device which printed the color sample.

Step S116 of the method illustrated in FIGS. 3 and 4 may be implemented in a computer program product that may be executed on a computer. The computer program product may be a tangible computer-readable recording medium on which a control program is recorded, such as a disk, hard drive, or may be a transmittable carrier wave in which the control program is embodied as a data signal. Common forms of computer-readable media include, for example, floppy disks, flexible disks, hard disks, magnetic tape, or any other magnetic storage medium, CD-ROM, DVD, or any other optical medium, a RAM, a PROM, an EPROM, a FLASH-EPROM, or other memory chip or cartridge, transmission media, such as acoustic or light waves, such as those generated during radio wave and infrared data communications, and the like, or any other medium from which a computer can read and use.

The exemplary processor 44 and method may be implemented on one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, or PAL, or the like. In general, any device, capable of implementing a finite state machine that is in turn capable of implementing the method of compensating measured hot colors for thermochromaticity errors.

Once the TCC model 40 has been built, steps S102 to S116 may be repeated at intervals to recalibrate the model.

Although the phrase "thermochromaticity" is commonly used to refer specifically to chromatic shift occurring in color pigments with change in temperature, in the present application, the errors between the measurements taken at a "just-fused" location within the output device, and when the print output had an opportunity to cool to ambient temperature are broadly grouped under the term "thermochromaticity error." For example, there may be shift in lightness component (i.e., $L^*$) of the color occurring when glossy images are cooled. Such kinds of shifts occurring due to change in temperature are all grouped as "thermochromaticity" errors.

As noted above, the exemplary TCC model 40 may be built using a training database containing the acquired "hot" and "cool" color measurements and area coverage information. In one embodiment, a simple weighted least squares algorithm may be used for generating a TCC matrix or matrices, based on the assigned weights. Construction and application of the matrix to various regions of the color space, based on area coverage information, enables a nonlinear correction to be applied to the color measurements by selective use of a single TCC matrix or multiple TCC matrices. Three exemplary methods for accounting for area coverage are described in further detail below, which include a simple binary method for conditionally applying the thermochromaticity compensation matrix when the area coverage meets a predetermined threshold, and more complex methods.

The three methods for generating the model 40 will now be described. An algorithm which can be adapted to all three methods is described below.

Method 1: A Binary Conditional Compensation Approach

In this approach, the compensation matrix applied at high area coverage is different from that applied at low area coverage. For example, a first compensation matrix $M_L$ (or no compensation matrix) is applied when the computed area coverage parameter is below a threshold value and a second, different compensation matrix $M_H$ is applied when the computed area coverage meets (is at or above) the threshold value. An appropriate threshold can be determined empirically. In one embodiment, the first compensation matrix $M_L$ applies no compensation for thermochromaticity, although it may apply a correction for sensor differences if the two sensors are different.

Experimental data may be used to identify a suitable threshold. Above the threshold, it is considered favorable to apply a single matrix thermochromaticity compensation technique. Applications utilizing color measurement data would conditionally apply the thermochromaticity compensation algorithm based on whether the requested color patch, whose CMYK values are known, falls above or below this density threshold.

Figure 5:
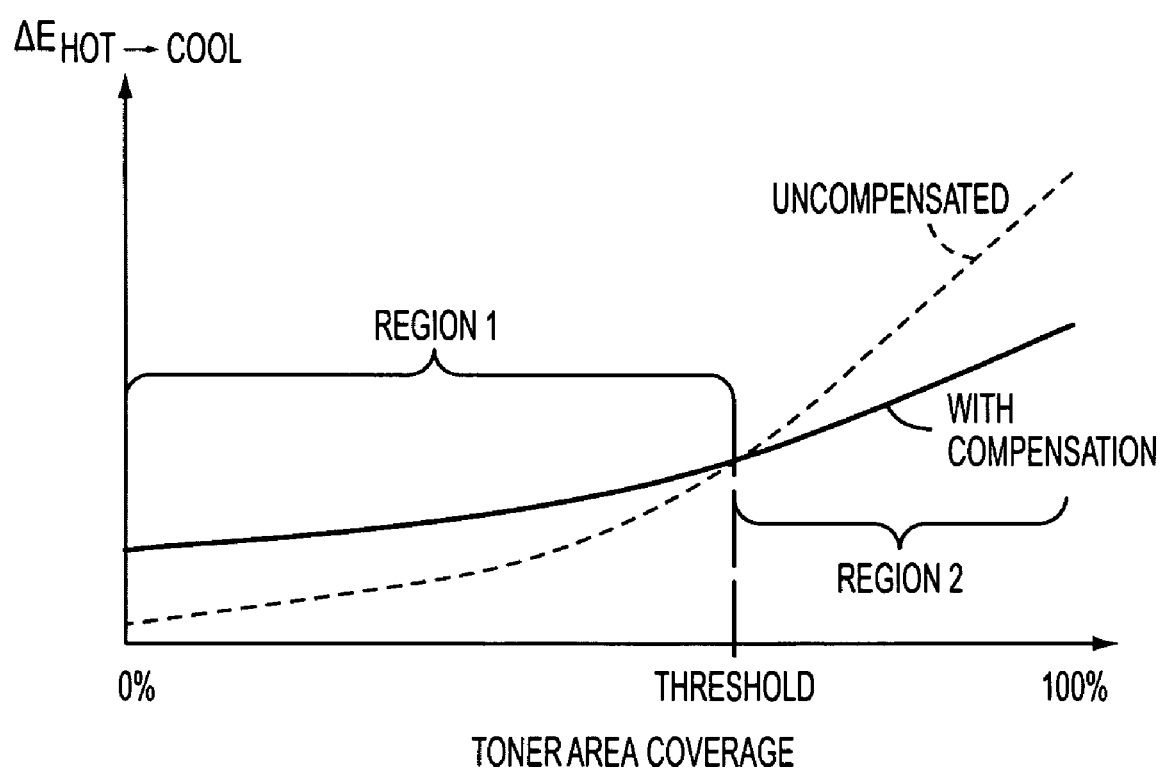
FIG. 5 illustrates a binary conditional correction scheme in accordance with one aspect of the exemplary method of FIGS. 3 and 4.

FIG. 5 schematically illustrates a plot of $\Delta E(hot{\rightarrow}cool)$ vs. area coverage (expressed on a scale of 0-100%). $\Delta E(hot{\rightarrow}cool)$ represents the empirically determined error when the hot measurements are converted to corresponding cool measurements. The curve labeled "uncompensated" shows the $\Delta E(hot{\rightarrow}cool)$ without applying a thermochromaticity correction. As it can be seen in this plot, the errors are quite low when the area coverage is low but rise as area coverage increases. The "with compensation" plot shows the errors when a chromaticity correction algorithm of the type described in application Ser. No. 11/737,576 (now U.S. Pat. No. 7,684,082) is applied. As can be seen, the error is slightly higher than when no compensation is applied when the area coverage is low. At higher area coverage, the "with compensation" plot shows lower errors than for the uncompensated plot. Method 1 of the exemplary embodiment therefore may define the threshold at or about the point at which the $\Delta E(hot{\rightarrow}cool)$ with compensation equals the uncompensated $\Delta E(hot{\rightarrow}cool)$ (the intersection of the two plots). In region 1, which includes all area coverages below the threshold, no thermochromaticity correction is applied. In region 2, which includes all area coverages above the threshold, the chromaticity correction algorithm is applied. The expected error, in method 1, is thus reduced in each region.

In this embodiment, a single TCC Matrix Q can be based on the hot and cool data from a color patch set which has a complete spread of toner area coverage (TAC) patches using an algorithm as described below, in which all weights are set to unity. The TCC Matrix is applied only to measurements of color patches that exceed the TAC threshold (region 2). No TCC is applied to measurements of patches that fall below TAC threshold (region 1). Thus for example, for test patches illustrated in FIG. 1, the low area coverage patches 28 may receive a different (or no) thermo-chromaticity correction from high area coverage patches 26.

Method 2: A Region Based Conditional Compensation Approach

In a second method, a set of regions are defined, based on area coverage, and the patch to be corrected is assigned to the most appropriate area coverage region. A thermochromaticity correction for that region can then be applied by the model.

Figure 6:
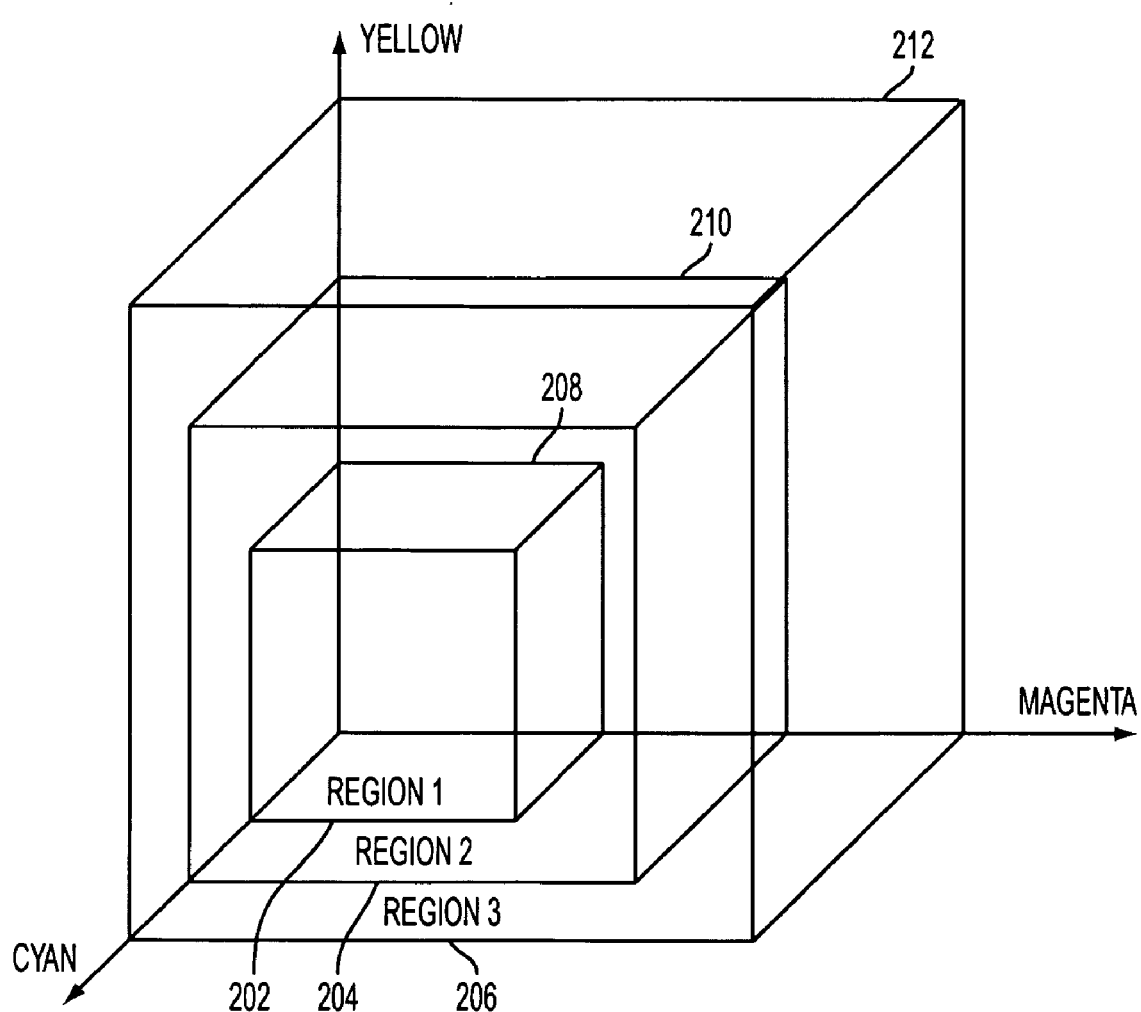
FIG. 6 illustrates a region based conditional thermo-chromaticity compensation scheme in accordance with another aspect of the exemplary method of FIGS. 3 and 4.

For example, in the second method, the color space for the color separations employed in the printing device (e.g., CMYK) is divided into a number of regions as a function of toner density (computed area coverage). FIG. 6 illustrates, by way of example, three regions 202, 204, 206 for three color separations CMY, for ease of illustration. Region 1 covers C, M, and Y values at the lower end of the toner density scale. Region 2 extends from a boundary 208 with Region 1 to a boundary 210 with Region 3, i.e., a mid region of toner densities, and Region 3 extends from the boundary 210 to the maximum values of the toner densities illustrated by boundary 212. While the three regions are illustrated as having boundaries 208, 210 which are cubic (equal density for each separation) it is to be appreciated that the boundaries between the regions 202, 204, 206 may assume other shapes. Additionally, any number of regions may be defined, such as 3, 4, 5, 6, 10, or more. Additionally, any number of color separations can be considered, such as 3, 4, 5, 6, or more.

In one embodiment, a cluster based approach may be used to cluster combinations of C, M, Y area coverage values (and optionally K or other colorants) into different regions. Then, when a new sample is to be assigned to one of the regions, the Euclidian distance between the new sample values and the nearest CMY point(s) in three (or more) dimensional space is determined. The region in which the point with the minimum Euclidian distance from the new sample point is located is assigned to the new sample.

For example, if a point in a three dimensional space represents 0.3 Y, 0.3 C, 0.3 M and is assigned to Region 1, and another point with coordinates 0.4 C, 0.4 Y and 0.2 M is assigned to Region 2, then a point which is (0.4C, 0.4Y, 0.0M)

is assigned to one of these regions, based on respective Euclidian distances to the points already assigned to a region.

Once the regions are defined, a thermo-chromaticity compensation matrix Q1, Q2, Q3 can be created for each coverage region 202, 204, 206, etc. The number of training samples, N, used in the TCC matrix creation for each region 202, 204, 206 can be different (i.e., N=N1 for region 1, N=N2 for region 2, etc.). For example, compensation matrix Q1 is created for light patches (region 1), Q2 for mid-density patches (region 2), and Q3 for dark patches (region 3). When new patches are to be compensated, the relevant matrix applicable to each patch that falls within that area coverage region is applied. When processing color measurement data, the TCC system identifies the requested color patch in terms of its density region, and then utilizes the corresponding thermo-chromaticity compensation matrix.

The generalized algorithm for constructing the matrices is given below. Several weighting schemes are proposed for applying this algorithm to method 2. In one embodiment, fixed weights are used for each region. In another embodiment, variable weights based on distance may be employed. The weights may vary as a function of wavelength.

Method 3: Gain Weighted Thermochromaticity Compensation Method

In this method, a gain function is applied to a global compensation matrix Q. The matrix Q can be similar that created for Region 2 in method 1. The gain function can be a function of area coverage, e.g., patch halftone dot density. This gain function is applied to the thermochromaticity compensation matrix, for example, by multiplying the matrix by the appropriate gain. The gain function may be in the form of an equation or lookup table that is experimentally determined. For the low densities (low computed area coverage) the gain may be near or equal to zero so that the thermo-chromaticity compensation is hardly applied. For higher densities, the gain approaches a maximum value, e.g., 1, so that the thermochromaticity compensation output by the compensation matrix is entirely applied.

In this embodiment, a single matrix Q is created for the entire training set. As for method 2, several approaches for weights exist. In one embodiment, a single weight is used for the entire training set. In other embodiment, variable weights, which may be based on wavelengths can be easily incorporated, depending on a desire to emphasize visually important colors.

For new samples, the single matrix Q is multiplied by a gain that is a function of halftone dot density (computed area coverage) and the correction output by the matrix is applied to the hot measurements.

Figure 7:
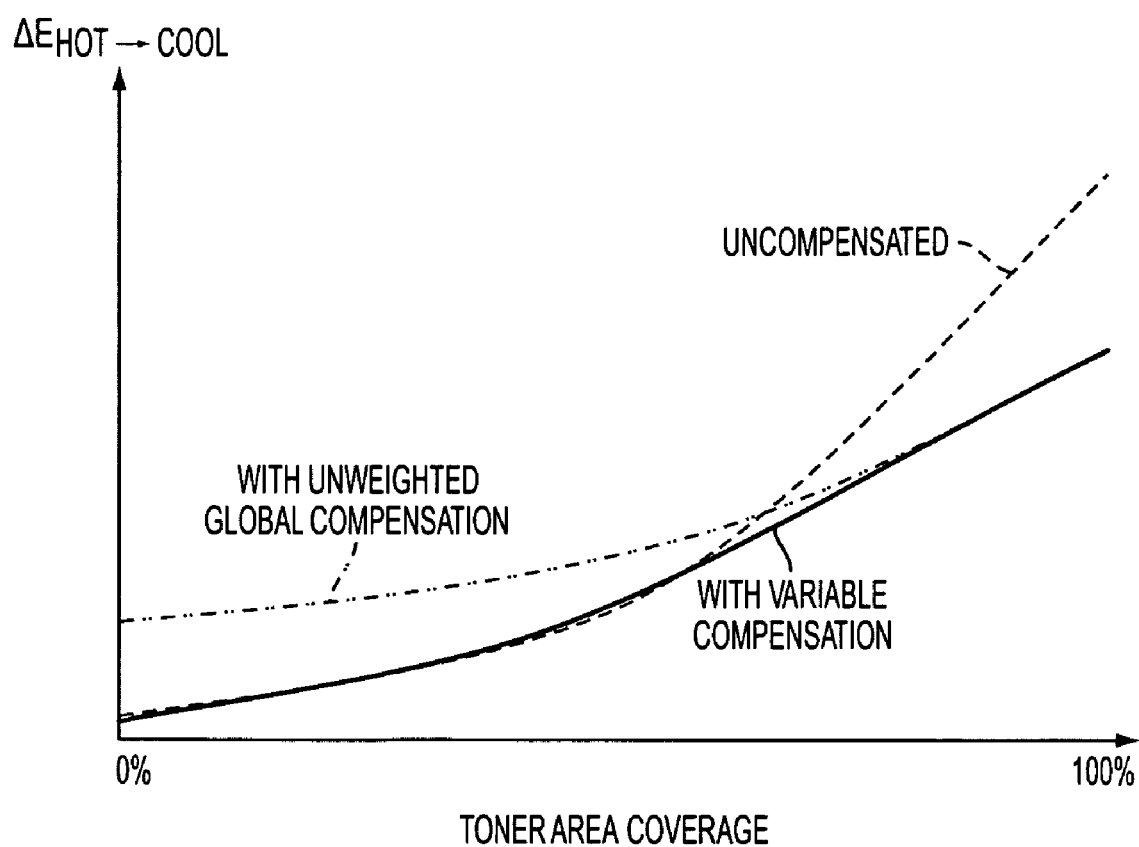
FIG. 7 illustrates a gain weighted thermochromaticity compensation method in accordance with another aspect of the exemplary method of FIGS. 3 and 4.

FIG. 7 illustrates the effect of applying a gain weighted (variable compensation) upon ΔE(hot→cool). As can be seen, the variable compensation plot provides a relatively low ΔE(hot→cool) throughout the range of area coverage by applying a linear gain to the global matrix which more closely mirrors the actual relationship between temperature change and toner coverage.

Figure 8:
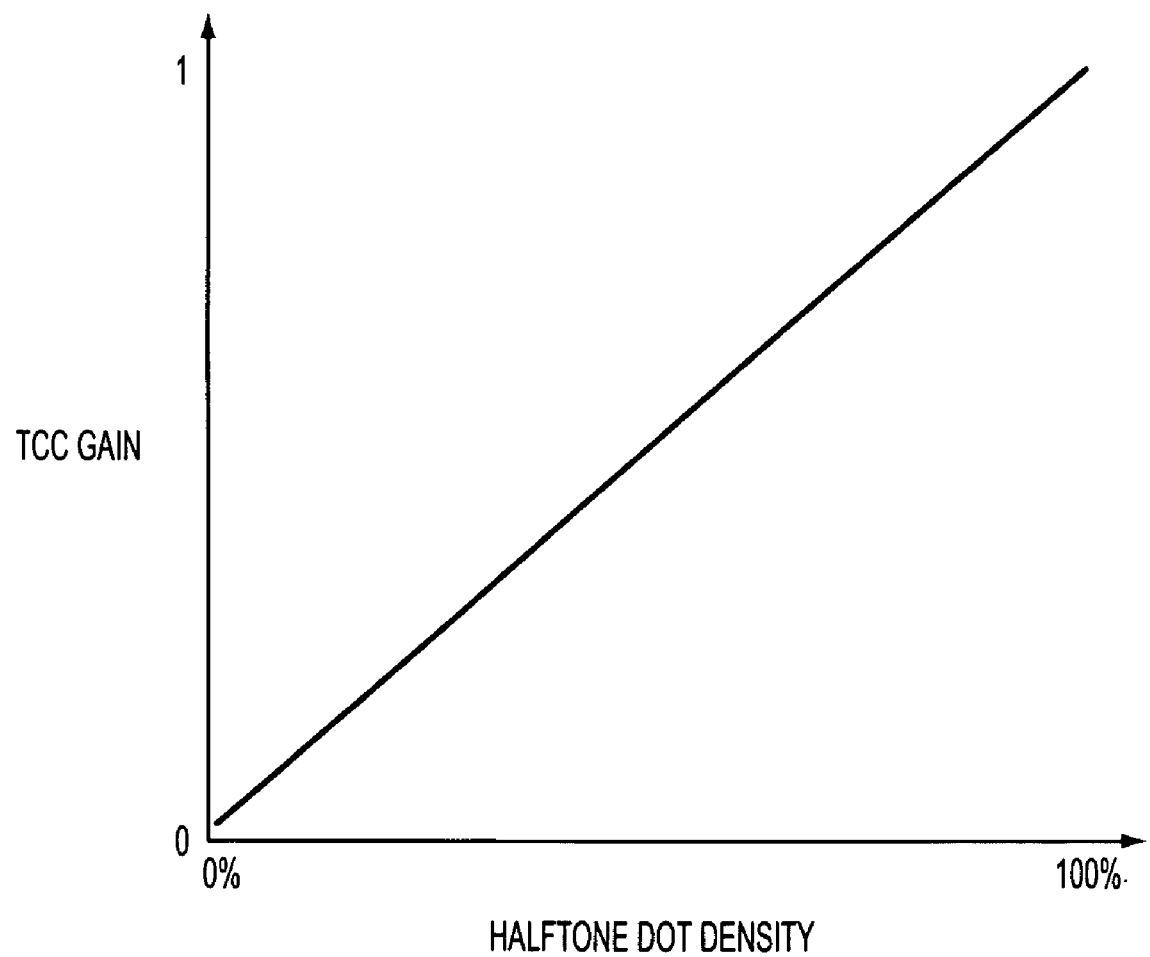
FIG. 8 illustrates an exemplary linear gain function.

FIG. 8 illustrates an exemplary gain function which may be applied in this method. The exemplary function is a linear function, which is dependent on the halftone dot density. As will be appreciated, the gain function may be non linear, e.g., exponential, stepped, or the like.

Weighted Least Squares Algorithm

The algorithm used to generate the TCC matrix 40 uses as input the hot and cool measurements stored in the database. The thermochromaticity matrix may be in the form of a transfer function or a look up table as a mapping from hot reflectance spectra (measured spectra of hot colors) to cool reflectance spectra (measured spectra of the same color samples after they are cooled to room temperature) using the same spectrophotometer or a different type of spectrophotometer.

The algorithm may be applied as follows. Let N represent a number of training spectral pairs. Each spectral pair corresponds to a test color sample as represented below in equation 1), which are available in the database, i.e., N represents the total number of thermochromaticity test colors (e.g., N is 2000). The object is to find the transformation $\Omega$ which describes the relationship between the cool measurements S and hot measurements R.

$$S = [S_1 \ S_2 \ \ldots \ S_N] \in \qquad \text{(Eqn. 1)}$$
$$R^{n \times N} \xrightarrow{\Omega} R = [R_1 \ R_2 \ \ldots \ R_N] \in R^{n \times N}$$

where $S_1 \ S_2 \ \ldots \ S_N$ are the vectors of the N cool spectral samples and $R_1 \ R_2 \ \ldots \ R_N$ are the corresponding vector elements for the hot spectral samples. Each vector includes n elements corresponding to spectral measurements (e.g., reflectance measurements, voltages, or other signals) at different wavelengths for the sample. For example, if the sensor includes an array of 31 LEDs (or other illumination sources), each having a respective peak wavelength, and the sensor separately measures reflectance for each of these sources to obtain 31 measurements, then n=31.

Assuming a linear, quadratic, or cubic affine, or the like for the relationship between the cool and hot training set, then a general expression for estimated cool spectral samples can be defined as follows:

$$S = QR \qquad \text{(Eqn. 2)}$$

In the present example, R is a 31×1 element vector for a linear model. The matrix Q, which is the TCC matrix, has a size 31×31. If an affine term is required, then the hot spectral colors are augmented with a scalar value of 1 to include the affine term. The resulting Q matrix will then be of size 31×32. If quadratic and cubic terms are added, then number of elements in vector R will correspondingly increase. To compute matrix Q accurately, a weighted error minimization in spectral space may be performed using a least squares minimization procedure. Matrix Q is then obtained by minimizing the objective function defined as:

$$J = \underset{Q}{\operatorname{argmin}} \sum_{i=1}^{N} w_i(\lambda) \| S_i(\lambda) - QR_i(\lambda) \|^2 \qquad \text{(Eqn. 3)}$$

where $w_i(\lambda)$ represents a weight, such as a wavelength dependent weight, or a fixed weight, e.g., 1.

$S_i(\lambda)$ represents the vectors of the N cool spectral samples $R_i(\lambda)$ represents the corresponding vectors for the hot spectral samples The weight or weights $w_i(\lambda)$ can be chosen based on one of the following criteria:

(a) Fixed weights $w_i(\lambda) = 1$ or any other suitable fixed weight chosen for all colors I=1, ..., N (b) Weights based on the Euclidian distance of the color/between colors The weight $w_i(\lambda)$ may be proportional to $$\frac{1}{d_i^x},$$

where $d_i$ is the Euclidean distance between colors (for any number of color separations) and x is the number of color separations, e.g., 4. Euclidean distance is also referred to as the L2-Norm of two vectors.

The solution to the above optimization problem can be easily obtained by setting the gradient of J with respect to Q equal to zero. This results in:

$$Q = AP^{-1} \qquad \text{(Eqn. 4)}$$

where $$A = \sum_{i=1}^{N} w_i(\lambda) S_i R_i^T, \text{ and } P = \sum_{i=1}^{N} w_i(\lambda) R_i R_i^T \qquad \text{(Eqn. 5)}$$

and T represents the transpose of the vector.

Once Q is computed, the estimated cool spectrum Ŝ of the target color measured by the sensor 14 is obtained by:

$$\hat{S} = QR \qquad \text{(Eqn. 6)}$$

where R is as previously defined, for the new color sample.

As will be appreciated, the same algorithm can be adapted for each of the three methods described above. In method 1, the weight $w_i(\lambda)$ is set to 1 and the algorithm used to compute a single matrix for use when a sample is classified in region 2. For method 1, therefore, the matrix Q can thus be obtained by minimizing the objective function defined as:

$$J = \underset{Q}{\arg\min} \sum_{i=1}^{N} 1 \|S_i(\lambda) - QR_i(\lambda)\|^2 \text{ and}$$

$$Q = \sum_{i=1}^{N} S_i R_i^T \left( \sum_{i=1}^{N} R_i R_i^T \right)^{-1}$$

In methods 2 and 3, different weights $w_i(\lambda)$ can be used, i.e., $$Q = \sum_{i=1}^{N} w_i(\lambda) S_i R_i^T \left( \sum_{i=1}^{N} w_i(\lambda) R_i R_i^T \right)^{-1}$$

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A method for estimating color measurements of color samples comprising:
    computing an area coverage of a color sample;
    printing the color sample;
    measuring a color of the printed color sample at a first temperature;
    estimating a color of the printed color sample at a second temperature lower than the first temperature, the estimation being based on the area coverage and a thermochromatic model which represents relationships between measured colors of printed color samples at the first and second temperatures.

2. The method of claim 1, wherein the computed area coverage is based on the halftone dot density of the color sample.

3. The method of claim 1, wherein the measuring of the color of the printed color sample at the first temperature includes measuring the color of the just-fused printed sample with an in-line spectral sensor.

4. The method of claim 1, wherein the measuring of the color of the printed color sample at the first temperature includes obtaining a set of measurements at different wavelengths.

5. The method of claim 1, further comprising, using the estimated color of the printed color sample at the second temperature as a basis for assessing operability of a color output device which printed the color sample.

6. The method of claim 1, wherein the thermochromatic model comprises a matrix and the estimating of the color of the printed color sample includes applying the matrix only when the computed area coverage meets a predetermined threshold area coverage.

7. The method of claim 1, wherein the thermochromatic model comprises a set of matrices, each matrix being assigned to an area coverage region and wherein the estimating of the color of the printed color sample includes applying a matrix from the set of matrices which is assigned to the area coverage region which includes the computed area coverage.

8. The method of claim 1, wherein the thermochromatic model comprises a matrix, and the method includes computing a gain factor based on the area coverage and applying the gain factor to the matrix.

9. The method of claim 1, wherein the thermochromatic model is generated by minimizing an objective function which is the sum, over a set of measured colors, of a function of the difference between measurements at the first and second temperatures.

10. The method of claim 9, wherein the thermochromatic model is generated by minimizing an objective function of the general form:

$$J = \underset{Q}{\arg\min} \sum_{i=1}^{N} w_i(\lambda) \|S_i(\lambda) - QR_i(\lambda)\|^2 \qquad \text{(Eqn. 3)}$$

where Q represents the matrix,
N represents a number of measured colors,
$w_i(\lambda)$ represents an optional wavelength dependent weight,
$S_i(\lambda)$ represents vectors of the N cool spectral samples, and
$R_i(\lambda)$ represents corresponding vectors for the N hot spectral samples.

11. The method of claim 1, wherein an area coverage is computed for each of a plurality of color separations.

12. The method of claim 1, wherein the color sample comprises one of a test patch and a customer image.

13. A computer program product comprising a non-transitory computer-readable recording medium encoding instructions, which when executed on a computer causes the computer to perform the method of claim 1.

14. A thermochromaticity compensation system comprising:

a spectral sensor which measures colors of printed color samples at a first temperature;

memory which stores a thermochromatic model which represents relationships between measured colors of printed color samples at the first temperature and measured colors of printed color samples at a second temperature as a function of a computed area coverage; and a processor which receives a measured color of a printed color sample from the spectral sensor at the first temperature, computes area coverage of the printed color sample, and accesses the model to estimate a color of the printed color sample at the second temperature based on the measured color and computed area coverage.

15. A color output device comprising the thermochromaticity compensation system of claim 14 and a marking engine which prints the printed color sample.

16. The color output device of claim 15, further comprising a source of area coverage information in communication with the processor, the processor computing the area coverage of the printed color sample based on the area coverage information.

17. An algorithmic method to compensate for thermochromaticity errors of in situ spectral color measurements of a color printing device comprising:

obtaining spectral measurements at a plurality of computed area coverage values of printed colors generated by the color printing device measured at a first temperature by an in-line spectrophotometer and at a second temperature;

generating a model, based on the spectral measurements, which maps spectral measurements at the first temperature to spectral measurements at the second temperature, as a function of area coverage;

measuring a selected color corresponding to a color input signal representing a desired color at the second temperature, wherein the selected color is measured at the first temperature by the in-line spectrophotometer;

computing an area coverage of the selected color; and applying the model to convert the measured color to a corresponding color when the measured color changes to the second temperature, based on the area coverage.

18. The method of claim 17, wherein the measuring comprises spectrophotometric measuring of just-fused prints by the in-line spectrophotometer in the color output device.

19. The method of claim 17, wherein the mapping comprises predetermining a thermochromaticity compensation matrix from empirical data including a set of sensor reflectance vectors.

20. The method of claim 17, further comprising assessing if the color is different from an expected color intended by the color input signal.

21. The method of claim 20, wherein the assessing comprises calibrating the color output device by adjusting an input signal to the color printing device corresponding to the measured in situ color in a manner wherein the in situ measuring of an output color corresponds to a desired output ambient color.

* * * * *